United States Patent [19]

Balko et al.

[11] Patent Number: 5,177,268
[45] Date of Patent: Jan. 5, 1993

[54] HYDRODEHALOGENATION OF AROMATIC COMPOUNDS

[75] Inventors: Edward N. Balko, Middletown; Jeffrey B. Hoke, North Brunswick; Gary A. Gramiccioni, Flemington, all of N.J.

[73] Assignee: Engelhard Corporation, Iselin, N.J.

[21] Appl. No.: 863,896

[22] Filed: Apr. 6, 1992

[51] Int. Cl.$^5$ .................. C07C 39/24; C07C 39/16
[52] U.S. Cl. .................. 568/726; 568/716; 568/725; 568/755; 568/776
[58] Field of Search ............ 568/716, 725, 726, 755, 568/774, 776

[56] References Cited

U.S. PATENT DOCUMENTS 4,280,012  7/1981  Pastura et al. .................. 568/755
4,618,686  10/1986  Boyer et al. .................. 568/726

FOREIGN PATENT DOCUMENTS 0001909  5/1979  European Pat. Off. ............ 568/726
55196  6/1982  European Pat. Off. .

OTHER PUBLICATIONS

Melody, M., "On The . . . Liability Encourages PCB Elimination in Transformers", Hazmat World, Feb. 1992, pp. 62-64.
Rodensky, R., et al., "Regulatory and Technological Trends in PCB Treatment and Disposal", Hazmat World, Feb. 1992, pp. 56-60.
Rylander, P., "Catalytic Hydrogenation Over Platinum Metals", Academic Press 1967, pp. 405-431.
Baltzly, et al., "The Catalytic Hydrogenation of Halogen Compounds", pp. 261-365, 1946.
Coq, et al., "Conversion of Chlorobenzene Over Palladium and Rhodium Catalysts", J. of Catalysts 101, 434-445 (1986).
Kawakami, et al., "Selectivity in Consecutive Hydrogenation of Chlorobenzene in Liquid Phase", 1975.
Mathe, et al., "Active Environment Protection: Hydrodehalogenation of Polychlorinated Compounds", Hazardous Waste: Detection, Control, Treatment, ed. by P. Abbou 1988, pp. 1615-1619.
Peeling, et al., "Effect of Amines on the Catalytic Hydrogenation of Chlorobenzene", Chemistry and Industry, 1958, pp. 362-363.
Kammerer, H., et al., "The Hydrogenation-Dehalogenation of Aromatic Hologen Compounds . . . ", Chem. Ber., 91, 1376-1379 (1958).
Chem. Abstracts, No. CA89(3): 23376d (1978).
Chem. Abstracts, No. CA87(3): 16747(f) (1977).
Chem. Abstracts, No. CA114(13): 121572u (1990).
Chem. Abstacts, No. CA114(12): 108253ww (1990).

Primary Examiner—Werren B. Lone
Attorney, Agent, or Firm—Stephen I. Miller

[57] ABSTRACT

A process for hydrodehalogenating halogenated aromatics present in a contaminated aqueous environmental source in which the halogenated aromatics are reacted with hydrogen gas or a source of hydrogen gas in the presence of a basic proton acceptor and a catalyst of palladium on carbon.

11 Claims, No Drawings ial applications.

HYDRODEHALOGENATION OF AROMATIC COMPOUNDS

FIELD OF THE INVENTION

The present invention is generally directed to the hydrodehalogenation of halogenated organic compounds in an aqueous medium in which the compounds are reacted with hydrogen or a source of hydrogen in the presence of palladium on a carbon substrate and a basic proton acceptor preferably under mild temperature and pressure conditions. The present invention is particularly suited for the removal of chlorinated aromatics such as chlorobenzenes and chlorinated phenols from aqueous contaminated environmental sources such as waste water and hazardous waste sites.

BACKGROUND OF THE INVENTION

The removal of halogenated organic compounds from aqueous environmental sources including halogenated aromatic compounds such as chlorophenols and chlorobenzenes has posed serious problems. Typically, the halogenated compounds have been disposed of by separating, such as by steam stripping, using a microporous hollow-fiber membrane, or carbon adsorption, the contaminants from their aqueous environment and then subjecting the resulting concentrated levels of contaminants to incineration. However, the combustion of halogenated aromatics may result in the production of highly toxic by-products such as dioxins. Thus, incineration can itself become an environmentally unsafe practice and its use for the disposal of halogenated phenols is problematical.

Industry has therefore looked to alternative techniques for the destruction of halogenated aromatics found in the environment. Among the techniques which have been studied are biological treatment and chemical dehalogenation.

Chemical dehalogenation methods have been developed as an alternative to incineration and land disposal because they convert the halogenated organic compounds to less toxic non-halogenated compounds, in the case of halogenated phenols to phenol itself. One such process employs a sodium naphthalene reagent to form sodium chloride and an inert sludge. While the sludge can be safely incinerated, the process is complicated by requiring an air-free reaction vessel which limits its application for on-site treatment of contaminated environmental sources. In another approach, a dechlorination reagent is formed by reacting an alkali metal with polyethylene glycol in the presence of heat and oxygen.

The above-mentioned processes, which involve the oxidative dechlorination of halogenated organic compounds, are generally highly sensitive to water. Such processes require a separation step to remove the halogenated compounds from the aqueous environment before they can be treated. In addition, elevated temperatures are often required to carry out the reaction [See S. Tabaei et al., "Dehalogenation of Organic Compounds" *Tetra. Let.* 32(24) pp. 2727–30 (September 1991); M. Uhlir et al., "Recovery of Biphenyl by Catalytic Hydrogenolysis of Chlorinated Biphenyl" *Chem. Abstr.* 114 (23): 228496Z; and processes referred to in N. Surprenant et al., "Halogenated Organic Containing Wastes" pp. 224–231 Noyes Data Corp. (1988)]. Accordingly, these processes have not been widely accepted for the decontamination of environmental sites.

There has been developed a reductive process for the dehalogenation of halogenated organic compounds. J. F. A. Kitchen, U.S. Pat. No. 4,144,152 discloses a process for the treatment of halogenated organic compounds with UV radiation and hydrogen in the absence of an oxidizing agent. While this process may be conducted in an aqueous environment, the requirement of a UV radiation reactor has made light activated reduction of chemicals (LARC) processes of the type disclosed in U.S. Pat. No. 4,144,152 of limited commercial value. Although numerous references to hydrodechlorination using a palladium on carbon catalyst have been reported in the technical literature [Rylander, P. N. "Catalytic Hydrogenation over Platinum Metals," Academic Press, New York, 1967, pp. 405–431] no comprehensive study on the complete dechlorination of chlorophenols or chlorobenzenes has been reported.

There is therefore a need for processes in which halogenated organic compounds can be removed directly from aqueous contaminated environmental sources in a safe and cost effective manner. Such processes should be able to be conducted under mild reaction conditions and be effective in treating contaminated sources having both very low and very high concentrations of contaminants as is likely to be found in a variety of waste streams.

SUMMARY OF THE INVENTION

The present invention is directed to a process of hydrodehalogenating halogenated organic compounds specifically halogenated phenols and benzenes and particularly those typically found in aqueous contaminated environmental sources such as waste streams and the ground water found at hazardous waste disposal sites. In accordance with the invention, the halogenated aromatics are removed directly from the aqueous environment, without the dangers of incineration or expensive radiation equipment, in a cost effective manner.

The concentration of the contaminants which may be treated in the present process can be in the parts per million (ppm) range. Specifically, the present invention can treat aqueous streams containing as little as 2 ppm of contaminants. Of course, the process described herein is effective in treating waste streams containing much higher concentrations of halogenated contaminants on the order of 1,000 ppm or more. While a typical aqueous waste stream may have a halogenated organic content of 100 ppm, the process of the invention may also be used to treat highly concentrated halogenated aromatics (e.g. ≧0.1%) as may be found at a hazardous waste disposal site. In order to facilitate the process of the invention when large amounts of concentrated halogenated aromatics are to be treated, an organic water-miscible co-solvent is typically employed. Such organic water-miscible co-solvents include the lower alcohols such as methyl alcohol, ethyl alcohol, propyl alcohol and the like, dioxane, tetrahydrofuran and other such suitable solvents. For purposes of the invention, the preferred water-miscible co-solvent is ethyl alcohol. The proper water/co-solvent concentrations are chosen to solubilize the particular halogenated aromatic or mixtures thereof to be treated. It is therefore within the skill of the art to choose the proper water/co-solvent concentrations. The co-solvent itself, particularly ethyl alcohol, with no added water may also be utilized.

In particular, the halogenated aromatics, particularly chlorinated phenols and chlorinated benzenes, are reacted in an aqueous medium with hydrogen gas or a source of hydrogen gas in the presence of a basic proton acceptor and a catalyst consisting essentially of palladium on a carbon substrate. The reaction may be conducted directly on an aqueous waste stream containing chlorinated aromatics without a prior separation step. In particular, halogenated phenols are thereby converted to phenol while halogenated benzenes are converted to benzene. A by-product of the reaction is hydrogen chloride which is produced in environmentally safe concentrations. The present invention therefore provides a safe and economically feasible method of treating sources of environmental pollution.

DETAILED DESCRIPTION OF THE INVENTION

The present invention is based on the surprising finding that halogenated benzenes and halogenated phenols, and in particular substituted and unsubstituted chlorinated phenols can be hydrodehalogenated in situ in an aqueous medium by reduction with hydrogen in the presence of a basic proton acceptor and a catalyst of palladium on a carbon substrate. As used herein "palladium" means elemental palladium or a palladium compound (e.g. palladium oxide) which ca be reduced in the presence of hydrogen gas or a source of hydrogen gas. Because carbon is hydrophobic, it was surprising to find that carbon could be used effectively as a substrate for palladium in an aqueous medium to dechlorinate halogenated phenols. The carbon substrates may be any of those customarily employed to support a noble metal catalyst. The amount of palladium metal on the carbon substrate is generally in the range of from 2 to 10% by weight, preferably about 5% by weight. Higher concentrations of palladium may be used, but any reaction rate increase is substantially offset by the increased cost of the palladium. The amount of the catalyst employed in the reaction varies depending on the concentration of halogenated hydrocarbon.

Hydrogen is supplied to the reaction as a gas or in the form of a compound capable of delivering hydrogen gas. The preferred compounds for this purpose are hydrazine, hydrazine compounds and borohydrides. The hydrazine compounds include, for example, hydrazine hydrate, hydrazine sulfate, hydrazine chloride and the like. Alkali metal borohydrides such as sodium borohydride and potassium borohydride are the preferred borohydride sources of hydrogen. The amount of hydrogen used in the reaction should be sufficient to replace the removed halogen substituents with hydrogen and is therefore at or above a stoichiometric amount.

In accordance with the invention, both hydrogen gas and other sources of hydrogen such as hydrazine and borohydrides can be used to hydrodehalogenate halogenated aromatics and particularly chlorophenols and chlorobenzenes.

A basic proton acceptor is also employed to assist the reaction and drive it to completion at a reasonable rate when the aqueous stream contains higher concentrations (e.g. $\geq 0.1\%$) of the halogenated aromatics. Examples of the basic proton acceptor include ammonium hydroxide, sodium hydroxide, sodium acetate and organic amines such as triethylamine. Ammonium hydroxide is the preferred proton acceptor. The proton acceptor is preferably added in an amount equal to or exceeding a stoichiometric amount.

The reduction reaction of the present invention is preferably conducted under mild temperature and pressure conditions. The temperature of the reaction may be as low as ambient temperature. The upper temperature is limited by the boiling point of the aqueous stream, the halogenated aromatics contained therein, and/or the type of reactor. The upper temperature limit is also established by the decomposition temperature of hydrazine (120° C.) and the other sources of hydrogen when they are used in the reaction. It is generally desirable to maintain the temperature of the reaction within the range of from ambient temperature to 50° C.

The reaction pressure is preferably maintained within the range of from atmospheric pressure to 50 psig. It is preferred to conduct the reaction at or near atmospheric pressure. On the other hand, if the reaction is conducted on waste streams containing more highly concentrated amounts of halogenated phenols, the reaction is preferably conducted at slightly elevated pressures of from 10 to 50 psig.

The present invention may be employed to hydrodehalogenate a wide variety of substituted and unsubstituted halogenated aromatics commonly found in contaminated environmental sources such as waste streams or the ground water found at hazardous waste disposal sites. Among the halogenated aromatics e.g., halogenated phenols and halogenated benzenes which are commonly associated with these sources are the chlorobenzenes, bromobenzenes, chlorophenols and bromophenols. More commonly the chlorophenols and chlorobenzenes are present. For purposes of the invention, the term halogenated phenols is intended to include the mono-, di-, tri-, tetra- and penta-halogenated phenols and all of the position isomers thereof. Similarly, the term halogenated benzenes is intended to include mono and multiple halo substituents as well as all possible position isomers. The invention is also intended to include the treatment of mixtures of the various halogenated phenols as well as halogenated benzenes.

The halophenols, particularly the chlorophenols have a number of commercial uses including antibacterial and germicidal agents, disinfectants and wood preservatives. Accordingly, large amounts of these toxic chemicals are employed in industry and in agriculture. Their disposal has become of major interest to government and industry alike who are concerned with protecting the environment from contamination with hazardous waste. The present invention provides a safe and economical means of detoxifying hazardous waste streams containing chlorophenols at the site of the contamination.

The types of reactors which may be used to carry out the process of the present invention are well known to those skilled in the art. Such reactors include fixed bed systems such as trickle-bed reactors, slurry bed reactors and the like. A discussion of the operation of such reactors and their structural components are described in P. A. Ramachandran et al. "Three-Phase Catalytic Reactors" (Gordon and Breach Science Publishers, 1983) and Charles Satterfeld, "Heterogenous Catalysis in Practice", Chap. XI, pp 312–369, McGraw Hill (1980), each incorporated herein by reference.

A trickle bed reactor generally includes a tube having a suitable catalyst such as a noble metal on a support packed along its entire length. The reactor has an inlet for receiving a liquid (e.g. a waste stream) and hydrogen gas which are brought into contact and mixed optionally in the presence of an inert material such as α-alumina. The liquid and hydrogen pass through the catalyst bed and the product from the bottom of the reactor.

The following examples are illustrative of embodiments of the invention and are not intended to limit the invention as encompassed by the claims forming part of the application.

EXPERIMENTAL

General Comments

All reactions per Examples I-X were carried out in a 1000 ml stainless steel Parr autoclave. A reduced 5% Pd/C catalyst was used in all reactions and was dried at 100° C. overnight and stored in a desiccator until used. A preferred catalyst, ECOCAT 1, is available from Engelhard Corporation, Iselin, N.J. Absolute ethanol (punctilious grade) was purchased from Quantum Chemicals and used as received. Water was distilled prior to use. 2-chlorophenol (2-CP), 3-chlorophenol(3-CP), 4-chlorophenol (4-CP), 2,3-dichlorophenol (2,3-DCP), 2,4-dichlorophenol (2,4-DCP), 2,5-dichlorophenol (2,5-DCP), 2,6-dichlorophenol (2,6-DCP), 3,4-dichlorophenol (3,4-DCP), 3,5-dichlorophenol (3,5-DCP), 2,4,5-trichlorophenol (2,4,5-TCP), 2,3,5-trichlorophenol (2,3,5-TCP), 2,4,6-trichlorophenol (2,4,6-TCP), 2,3,6-trichlorophenol (2,3,6-TCP), pentachlorophenol (PCP), 1,2-dichlorobenzene, 1,3-dichlorobenzene, 1,4-dichlorobenzene, 1,2,3-trichlorobenzene, 1,2,4-trichlorobenzene, 1,3,5-trichlorobenzene, 1,2,4,5-tetrachlorobenzene, hydrazine sulfate, and triethylamine were all purchased from Aldrich and used as received. Hydrazine hydrate (Hyd. Hyd.), sodium hydroxide (reagent grade), and sodium acetate were purchased from Fisher and used as received. Concentrated ammonium hydroxide (14.8M - Corco) was purged with ammonia (Aldrich) prior to each use.

Chlorophenol conversions during hydrodechlorination were measured by gas chromatography (GC) using a Hewlett Packard 5890 GC equipped with an FID and HP-1 methyl silicone capillary column. Samples were extracted from the reactor, filtered, and then mixed 1:1 with a solution of 1% nonane (internal standard) and 4% acetic acid (pH adjust) in ethanol. Due to the low sensitivity of chlorinated organic compounds for FID analysis, conversion calculations were based on the amount of phenol formed during the course of the reactions. Experimental error in analysis was approximately 1-2%.

EXAMPLE I

Hydrogen Reduction of 4-Chlorophenol (General Procedure)

A 1000 ml Parr autoclave was charged in air with 5.00 g (38.9 mmol) of 4-chlorophenol, 2.9 ml (42.9 mmol) of $NH_4OH$, 0.225 g ECOCAT 1 (dried at 100° C.), and 500 ml of ethanol. The autoclave was then sealed and connected to a gas delivery system containing a gas manifold, a gas regulator for maintaining constant hydrogen pressure within the autoclave, and a calibrated, 500 ml gas reservoir for monitoring hydrogen consumption during the course of reaction. (Typically, reservoir pressure was maintained at 70 psi while autoclave pressure was maintained at 35 psi.) The gas delivery system (manifold and reservoir) was charged and vented three times with argon and then charged a fourth time with argon. The autoclave then was purged with argon in a similar manner and heated under pressure to 35° C. via an external, constant temperature bath. Subsequently, the gas delivery system and autoclave were purged with hydrogen (zero grade) by the same charge/vent procedure described previously. After charging the autoclave the fourth time with hydrogen, mechanical stirring was started (520 rpm), and the reservoir was isolated from the tank gas supply via a shut-off valve in the manifold system. Pressure drop over time in the gas reservoir was monitored via a strip chart recorder and digital pressure readout. The initial rate over the first 1.2 minutes of reaction was obtained from the hydrogen consumption curve, and a quantitative phenol yield was determined by GC analysis of an extracted sample. Results are summarized in Table I.

EXAMPLE II

Hydrogen Reductions of Other Chlorophenols

Using the same procedure described in Example I, 4-chlorophenol, 2-chlorophenol (5.00g, 38.9 mmol), 3-chlorophenol (5.00 g, 38.9 mmol), 2,3-dichlorophenol (3.18 g, 19.5 mmol), 2,4-dichlorophenol (3.18 g, 19.5mmol), 2,5-dichlorophenol (3.18 g, 19.5 mmol), 2,6-dichlorophenol (3.18 g, 19.5 mmol), 3,4-dichlorophenol (3.18 g, 19.5 mmol), 3,5-dichlorophenol (3.18 g, 19.5 mmol), 2,3,5-trichlorophenol (2.57 g, 13.0 mmol), 2,3,6-trichlorophenol (2.57 g, 13.0 mmol), or 2,4,6-trichlorophenol (2.57 g, 13.0 mmol) were hydrodechlorinated over 0.225 g of ECOCAT 1 and 2.9 ml (42.9 mmol) of $NH_4OH$ in 500 ml of ethanol. To ensure complete conversions, 2,4,5-trichlorophenol (2.57 g, 13.0 mmol) and pentachlorophenol (2.08 g, 7.8 mmol) were reacted with larger amounts of ammonium hydroxide, 5.4 ml (80.0 mmol) and 8.4 ml (124.3 mmol), respectively. To facilitate initial rate comparisons between various chlorophenols, the amount of substrate reacted was standardized to 39 mmol of liberated chloride. Results are summarized in Table I.

EXAMPLE III

Hydrogen Reduction of 4-Chlorophenol with Other Bases

Using the procedure described in Example I, 5.00 g (38.9 mmol) of 4-chlorophenol was hydrodechlorinated over 0.150 g of ECOCAT 1 and either 2.9 ml (38.9 mmol) of ammonium hydroxide, 1.71 g (38.9 mmol) of sodium hydroxide, 5.82 g (38.9 mmol) of sodium acetate, or 6.0 ml (42.8 mmol) of triethylamine in 500 ml of ethanol. Initial rates over the first 1.2 minutes were 3.84, 3.64, 1.01, and 0.0 mmol/min, respectively. Phenol yields (reaction time in parentheses) were ≧99% (60 min.), 79% (65 min.), 76% (70 min.), and 1% (200 min.), respectively.

EXAMPLE IV

4-Chlorophenol Aging Study

A 500 ml Parr shaker bottle was charged with 3.0 g (23.3 mmol) of 4-chlorophenol, 3.6 ml (53.3 mmol) of $NH_4OH$, 0.506 g of ECOCAT 1, and 300 ml of a 50:50 ethanol-water mixture. The bottle was attached to the shaker apparatus, charged and vented four times with argon, and then charged and vented three times with hydrogen. Subsequently, the bottle was charged a fourth time with hydrogen (24 psi) and the shaker was activated. After 30 minutes, the reaction was stopped, the apparatus was vented, and the reaction mixture was filtered through a 0.45 micron nylon filter disk. (The first few milliliters of filtrate collected were used for GC analysis to calculate a quantitative phenol yield.) The filtered catalyst was washed with water (3×250 ml) and ethanol (3×250 ml), and sucked dry for at least 2 hours. The dried catalyst then was re-used for the next run in the study using fresh substrate and following the same procedure just described. After the 16th thirty minute run, 4-chlorophenol conversion was 97%. A similar aging study using ethanol as the solvent resulted in a 4-chlorophenol conversion of only 6% after six 90 minute reaction cycles.

EXAMPLE V

Hydrogen Reduction of 4-Chlorophenol in Other Solvents

Using the procedure described in Example I, 5.00 g of 4-chlorophenol was hydrodechlorinated over 0.225 g of ECOCAT 1 and 2.9 ml (42.9 mmol) of NH$_4$OH in either 500 ml of water or 500 ml of a 50:50 ethanol-water mixture. Results are summarized in Table II.

EXAMPLE VI

Hydrogen Reduction of Other Chlorophenols in 50:50 Ethanol-Water

Using the procedure described in Example I, 2,4-dichlorophenol (3.18 g, 19.5 mmol), 2,4,5-trichlorophenol (2.57 g, 30.0 mmol), or pentachlorophenol (2.08 g, 7.8 mmol) were hydrodechlorinated over 0.225 g of ECOCAT 1 and 3.1 ml (44.6 mmol) of NH$_4$OH in 500 ml of a 50:50 ethanol-water mixture. A 50° C. reaction temperature was required to hydrodechlorinate pentachlorophenol at a reasonably fast rate. Results are summarized in Table II.

EXAMPLE VII

Hydrazine Hydrate Reduction of 4-Chlorophenol in Various Solvents

A 1000 ml Parr autoclave was charged in air with 5.00 g (38.9 mmol) of 4-chlorophenol, 4.3 ml (63.6 mmol) of NH$_4$OH, 0.225 g of ECOCAT 1, 2.70 g (85% w/w, 45.8 mmol) of hydrazine hydrate, and 500 ml of either ethanol, water, or a 50:50 ethanol-water mixture. The autoclave was sealed but not pressurized, and mechanical stirring (520 rpm) was begun immediately. The reaction mixture was sampled periodically and its composition was assayed by gas chromatography. Quantitative phenol yield as a function of time was determined by GC, and the data was fit to a simple first order kinetic expression. Results are summarized in Table III.

EXAMPLE VIII

Hydrazine Hydrate Reduction of Other Chlorophenols

Using the procedure described in Example VII 3,5-dichlorophenol (3.18 g, 19.5 mmol), 2,4,5-trichlorophenol (2.57 g, 13.0 mmol), or pentachlorophenol (2.08 g, 7.8 mmol) were hydrodechlorinated over 0.225 g of ECOCAT 1, 2.71 g (85% w/w, 45.8 mmol) of hydrazine hydrate, and 4.2 ml (62.1 mmol) of NH$_4$OH in 500 ml of a 50:50 ethanol-water mixture. A 50° C. reaction temperature was required to hydrodechlorinate pentachlorophenol at a reasonably fast rate. Results are summarized in Table III.

EXAMPLE IX

Hydrazine Sulfate Reduction of 4-Chlorophenol and Pentachlorophenol

Using the procedure described in Example VIII, 5.00 g (38.9 mmol) of 4-chlorophenol was hydrodechlorinated over 0.225 g of ECOCAT 1, 5.47 g (42.0 mmol) of hydrazine sulfate, and 12.0 ml (177.6 mmol) of NH$_4$OH in 500 ml of a 50:50 ethanol-water mixture or 2.08 g (7.8 mmol) of pentachlorophenol was hydrodechlorinated over 0.225 g of ECOCAT 1, 5.99 g (46.1 mmol) of hydrazine sulfate, and 14.2 ml (210.1 mmol) of NH$_4$OH in 500 ml of a 50:50 ethanol-water mixture. Results are summarized in Table III.

EXAMPLE X

Autoclave Dechlorination of Chlorobenzenes

In the following trials, a sufficient quantity of the chlorobenzene was dissolved in 500 ml ethanol to yield a solution which contained 0.26 gram-moles of chlorine per liter as the organic compound. Eighteen grams of 29% (W/W) aqueous ammonia solution were then added and the hydrodechlorination reactions were carried out using 500 mg. of Ecocat-1, 4 atmospheres hydrogen pressure, and 30° Celsius. The following initial rates were measured:

| Compound | Initial Rate mmoles (g cat-sec)$^{-1}$ |
| --- | --- |
| Chlorobenzene | 0.28 |
| 1,2-dichlorobenzene | 0.20 |
| 1,3-dichlorobenzene | 0.18 |
| 1,4-dichlorobenzene | 0.09 |
| 1,2,3-trichlorobenzene | 0.16 |
| 1,2,4-trichlorobenzene | 0.09 |
| 1,3,5-trichlorobenzene | 0.09 |
| 1,2,4,5-tetrachlorobenzene | 0.03 |

One hour reaction time was found sufficient to convert at least 99% of all of these halogenated materials to benzene.

EXAMPLE XI

Shaker Reactor Dechlorinations

As it yields all three dichloro isomers as intermediates, 1,2,4-trichlorobenzene was the substrate used for several exhaustive dechlorination experiments in a shaker-type hydrogenation reactor. Fifty-six millimoles of the trichlorobenzene, 500 mg. of Ecocat-1, and twice the stoichiometric quantity of ammonium hydroxide (as the 29% aqueous solution) were combined with 300 milliliters of ethanol and the reaction run for 180 minutes at 2.7 atm hydrogen pressure and room temperature. At the end of that time, 99.2% of the trichlorobenzene, and 98.5% of the carbon-chlorine bonds originally present, had been consumed. Non-reacted trichlorobenzene and paradichlorobenzene, the least reactive of the intermediates Example X were the principal halogenated organic remaining in the ethanol solution.

TABLE I

| HYDROGEN REDUCTION DATA FOR CHLOROPHENOLS IN ETHANOL | | | | | | |
| --- | --- | --- | --- | --- | --- | --- |
| CHLOROPHENOL | REDUCTANT | SOLVENT | BASE | TEMP. | PHENOL YIELD | RXN TIME |
| 2-CP | H$_2$ | EtOH | NH$_4$OH | 35° C. | ≥99% | 60 min. |
| 3-CP | H$_2$ | EtOH | NH$_4$OH | 35° C. | ≥99% | 120 min. |
| 4-CP | H$_2$ | EtOH | NH$_4$OH | 35° C. | ≥99% | 30 min. |
| 2,3-DCP | H$_2$ | EtOH | NH$_4$OH | 35° C. | ≥98% | 120 min. |

TABLE I-continued

HYDROGEN REDUCTION DATA FOR CHLOROPHENOLS IN ETHANOL

| CHLOROPHENOL | REDUCTANT | SOLVENT | BASE | TEMP. | PHENOL YIELD | RXN TIME |
|---|---|---|---|---|---|---|
| 2,4-DCP | $H_2$ | EtOH | $NH_4OH$ | 35° C. | ≧99% | 60 min. |
| 2,5-DCP | $H_2$ | EtOH | $NH_4OH$ | 35° C. | ≧99% | 205 min. |
| 2,6-DCP | $H_2$ | EtOH | $NH_4OH$ | 35° C. | ≧99% | 135 min. |
| 3,4-DCP | $H_2$ | EtOH | $NH_4OH$ | 35° C. | 91% | 135 min. |
| 3,5-DCP | $H_2$ | EtOH | $NH_4OH$ | 35° C. | ≧99% | 240 min. |
| 2,3,5-TCP | $H_2$ | EtOH | $NH_4OH$ | 35° C. | 87% | 90 min. |
| 2,3,6-TCP | $H_2$ | EtOH | $NH_4OH$ | 35° C. | ≧98% | 180 min. |
| 2,4,5-TCP | $H_2$ | EtOH | $NH_4OH$ | 35° C. | ≧99% | 22 hr. |
| 2,4,6-TCP | $H_2$ | EtOH | $NH_4OH$ | 35° C. | ≧99% | 180 min. |
| PCP | $H_2$ | EtOH | $NH_4OH$ | 35° C. | ≧98% | 83 hr. |

TABLE II

HYDROGEN REDUCTION DATA FOR CHLOROPHENOLS IN OTHER SOLVENTS

| CHLOROPHENOL | REDUCTANT | SOLVENT | BASE | TEMP | PHENOL YIELD | RXN TIME |
|---|---|---|---|---|---|---|
| 4-CP | $H_2$ | $EtOH/H_2O$ | $NH_4OH$ | 35° C. | ≧99% | 60 min |
| 2,4-DCP | $H_2$ | $EtOH/H_2O$ | $NH_4OH$ | 35° C. | ≧99% | 30 min |
| 2,4,5-TCP | $H_2$ | $EtOH/H_2O$ | $NH_4OH$ | 35° C. | 91% | 210 min |
| PCP | $H_2$ | $EtOH/H_2O$ | $NH_4OH$ | 50° C. | 70% | 20 hrs. |
| 4-CP | $H_2$ | $H_2O$ | $NH_4OH$ | 35° C. | ≧99% | 60 min. |

TABLE III

HYDRAZINE REDUCTION DATA FOR CHLOROPHENOLS

| CHLOROPHENOL | REDUCTANT | SOLVENT | BASE | TEMP | PHENOL YIELD | RXN TIME |
|---|---|---|---|---|---|---|
| 4-CP | Hyd. Hyd. | $EtOH/H_2O$ | $NH_4OH$ | 25° C. | ≧99% | 21 hr. |
| 3,5-DCP | Hyd. Hyd. | $EtOH/H_2O$ | $NH_4OH$ | 25° C. | ≧98% | 24 hr. |
| 2,4,5-TCP | Hyd. Hyd. | $EtOH/H_2O$ | $NH_4OH$ | 25° C. | ≧99% | 24 hr. |
| PCP | Hyd. Hyd. | $EtOH/H_2O$ | $NH_4OH$ | 50° C. | ≧99% | 23 hr. |
| 4-CP | Hyd. Hyd. | $H_2O$ | $NH_4OH$ | 25° C. | ≧99% | 21 hr. |
| 4-CP | Hyd. Hyd. | EtOH | $NH_4OH$ | 25° C. | 91% | 25 hr. |
| 4-CP | Hyd. Sulf. | $EtOH/H_2O$ | $NH_4OH$ | 25° C. | ≧99% | 21 hr. |
| PCP | Hyd. Sulf. | $EtOH/H_2O$ | $NH_4OH$ | 50° C. | 97% | 28 hr. |

We claim:

1. A method of hydrodehalogenating halogenated phenols, halogenated benzenes and mixtures thereof present in a substantially aqueous medium comprising treating said medium with hydrogen gas or a source of hydrogen gas in the presence of a basic proton acceptor and a catalyst consisting essentially of palladium on a carbon substrate.

2. The method of claim 1 wherein the reaction is conducted at a pressure of from atmospheric pressure to 50 psig.

3. The method of claim 1 wherein the reaction is conducted at a temperature of from ambient temperature to 50° C.

4. The method of claim 1 wherein the basic proton acceptor is ammonium hydroxide.

5. The method of claim 4 wherein the amount of the basic proton acceptor is equal to or in excess of a stoichiometric amount.

6. The method of claim 1 comprising treating said medium with an amount of hydrogen gas equal to or in excess of a stoichiometric amount.

7. The method of claim 1 wherein the source of hydrogen gas is selected from the group consisting of hydrazine, hydrazine hydrate, hydrazine salts and borohydrides.

8. The method of claim 1 wherein the halogenated phenols are chlorophenols.

9. The method of claim 1 wherein the halogenated benzenes are chlorobenzens.

10. A method of hydrodehalogenating halogenated phenols, halogenated benzenes, and mixtures thereof in a substantially aqueous contaminated waste stream suspected of containing halogenated phenols and halogenated benzenes comprising passing the waste stream into contact with hydrogen gas or a source of hydrogen gas selected from hydrazine, hydrazine hydrate, hydrazine salts and borohydrides in the presence of a basic proton acceptor and a catalyst consisting essentially of palladium on a carbon substrate at a temperature of from ambient temperature to 50° C. and at a pressure of from atmospheric pressure to 50 psig.

11. The method of claim 9 wherein the basic proton acceptor is ammonium hydroxide.

* * * * *